United States Patent [19]
Cohen

[11] Patent Number: 5,810,588
[45] Date of Patent: *Sep. 22, 1998

[54] CLAMPING DEVICE PARTICULARLY USEFUL FOR DENTAL HANDPIECES

[76] Inventor: Yechiel Cohen, 4 Rotem Street, Carmiel 20100, Israel

[*] Notice: The term of this patent shall not extend beyond the expiration date of Pat. No. 5,549,474.

[21] Appl. No.: 701,506

[22] Filed: Aug. 22, 1996

Related U.S. Application Data

[63] Continuation-in-part of Ser. No. 315,859, Sep. 30, 1994, Pat. No. 5,549,474.

[30] Foreign Application Priority Data

Oct. 6, 1993 [IL] Israel ........................................ 107202

[51] Int. Cl.⁶ .................................................. A61C 1/14
[52] U.S. Cl. ...................... 433/129; 433/132; 279/43.4
[58] Field of Search ................................... 433/127, 129, 433/132; 279/2.04, 43.2, 43.4, 46.1, 46.3, 46.4, 51

[56] References Cited

U.S. PATENT DOCUMENTS

| | | |
|---|---|---|
| Re. 10,115 | 5/1882 | Phillips . |
| 255,020 | 3/1882 | Rehfuss . |
| 1,701,172 | 2/1929 | Brown . |
| 2,670,963 | 3/1954 | Osborn .................................. 279/46.3 |
| 3,035,845 | 5/1962 | Benjamin . |
| 3,074,167 | 1/1963 | Turchi et al. . |
| 3,175,293 | 3/1965 | Borden . |
| 3,252,719 | 5/1966 | Borden . |
| 3,314,153 | 4/1967 | Maurer . |
| 3,448,850 | 6/1969 | Segel et al. . |
| 3,798,776 | 3/1974 | Lentine et al. . |
| 3,869,796 | 3/1975 | Thorburn . |
| 3,888,008 | 6/1975 | Lake et al. . |
| 3,947,966 | 4/1976 | Lieb et al. . |
| 3,955,284 | 5/1976 | Balson . |
| 4,114,276 | 9/1978 | Malata et al. ........................... 408/226 |
| 4,279,597 | 7/1981 | Grimm .................................... 433/129 |
| 4,406,470 | 9/1983 | Kataoka et al. ........................ 433/127 |
| 4,484,892 | 11/1984 | Pernot et al. ........................... 433/118 |
| 4,493,645 | 1/1985 | Nakanishi ............................... 433/129 |
| 4,536,157 | 8/1985 | Maizenberg ............................ 433/129 |
| 4,575,338 | 3/1986 | Maizenberg ............................ 433/126 |
| 4,578,034 | 3/1986 | Shibata et al. .......................... 433/126 |
| 4,595,363 | 6/1986 | Nakanishi ............................... 433/129 |
| 4,661,060 | 4/1987 | Strohmaier ............................... 433/82 |
| 4,781,589 | 11/1988 | Bareth .................................... 433/127 |
| 4,874,314 | 10/1989 | Fleer et al. ............................. 433/129 |
| 5,022,857 | 6/1991 | Matsutani et al. ........................ 433/85 |
| 5,040,980 | 8/1991 | Heil ....................................... 433/127 |
| 5,074,789 | 12/1991 | Shibata .................................. 433/129 |
| 5,090,906 | 2/1992 | Pernot ................................... 433/127 |
| 5,252,067 | 10/1993 | Kakimoto ............................... 433/129 |
| 5,254,004 | 10/1993 | Feldman et al. ....................... 433/129 |
| 5,549,474 | 8/1996 | Cohen .................................... 433/129 |

FOREIGN PATENT DOCUMENTS

| | | |
|---|---|---|
| 420169 | 4/1991 | European Pat. Off. . |
| 470324 | 2/1992 | European Pat. Off. . |
| 505888 | 5/1993 | European Pat. Off. . |
| 2557220 | 6/1985 | France . |
| 9210742 | 11/1992 | Germany . |
| 567170 | 1/1945 | United Kingdom . |

OTHER PUBLICATIONS

Patent Abstract of Japan, vol. 015, No. 403 (C–875) 15 Oct. 1991 & JP–A–03 165 755 (Morita Tokyo Seiskusho) 17 Jul. 1991.

Patent Abstract of Japan, vol. 013, No. 592 (C–671) 26 Dec. 1989 & JP–A–01 250 247 (Yoshida Dental Mfg) 5 Oct. 1989.

Patent Abstract of Japan, vol. 015., No. 403 (C–875) 15 Oct. 1989 & JP–A–03 165 756 (Morita Tokyo Seisakusho) 17 Jul. 1989.

*Primary Examiner*—Cary E. O'Connor

[57] ABSTRACT

A clamping device for clamping a rodlike member to a housing, particularly a dental tool to a handpiece, includes a tapered sleeve and a tapered collet received within the tapered sleeve, both having open ends for receiving the rodlike member. A depressible button is engageable with the closed end of the tapered collet to move the collet outwardly of the tapered sleeve, thereby to expand the tapered collet and to permit removal or insertion of the rodlike member. Several improved versions are also described including an annular seal carried by the open end of the tapered sleeve, a coiled spring urging the tapered collet inwardly of the tapered sleeve, an air bearing rotatably mounting an air turbine and the tapered sleeve, etc.

20 Claims, 9 Drawing Sheets

CLAMPING DEVICE PARTICULARLY USEFUL FOR DENTAL HANDPIECES

RELATED APPLICATION

The present application is for a continuation-in-part of my patent application Ser. No. 08/315,859, filed Sep. 30, 1994, now U.S. Pat. No. 5,549,474.

FIELD AND BACKGROUND OF THE INVENTION

The present invention relates to clamping devices for clamping a rodlike member to a housing. The invention is particularly useful in dental handpieces for clamping the shaft of a dental tool, such as a bur or drill, to the handpiece, and the invention is therefore described below with respect to this application.

One form of dental handpiece to which the invention is especially suitable is an air turbine handpiece for driving a dental tool, such as a bur or drill, at extemely high speeds, e.g. of the order of 400,000 rpm. In the existing air turbine handpieces, the clamping devices for clamping the dental tool shaft are generally of relatively bulky construction which increases the size and weight of the handpiece, and/or requires relatively awkward manipulations in order to remove and insert the dental tool into the handpiece.

OBJECTS AND BRIEF SUMMARY OF THE INVENTION

An object of the invention of the present application is to provide clamping devices for clamping a rodlike member to a housing, particularly a dental tool to a dental handpiece, which clamping devices may be embodied in a relatively simple, lightweight construction that can be conveniently manipulated in order to remove and insert the rodlike member. A more particular object of the invention of the present application is to provide clamping devices, especially dental handpieces, having a number of advantages over the clamping device and dental handpiece described in the above-cited patent application Ser. No. 08/315,859, as will be described more particularly below.

My patent application Ser. No. 08/315,859 disclosed a clamping device for clamping a rodlike member to a housing, comprising a tapered sleeve carried by the housing and having an inner diameter which decreases from an open end thereof to its opposite end; and a tapered collet received within the open end of the tapered sleeve. The tapered collet has an open end for receiving the rodlike member, and an outer diameter which decreases from its open end to its opposite end. The tapered collet is formed with an axial slit starting from its open end and extending along at least a part of its length, permitting said part to contract in diameter in order to firmly clamp the rodlike member when received in the tapered collet and the tapered collet is received within the tapered sleeve. A depressible button is carried by the housing and has an inner surface engageable with the opposite end of the tapered collet, and an outer surface engageable by a user to depress the button. A spring normally urges the button outwardly of the housing but is depressible to move the tapered collet outwardly of the tapered sleeve, thereby to expand the part of the tapered collet to permit removal of the rodlike member from the tapered collet, or insertion of the rodlike member into the tapered collet. When the rodlike member has thus been inserted into the tapered collet, it is firmly clamped by manually pressing it and the tapered collet into the tapered sleeve.

According to one preferred feature of the invention in the present application, the open end of the tapered collet terminates short of the open end of the tapered sleeve; and an annular seal is carried by the tapered sleeve between its open end and the open end of the tapered collet, the annular seal being coaxial with the tapered sleeve for receiving the rodlike member.

According to more specific aspects of this feature, the annular seal is wedged within the outer end of the tapered sleeve and has an outer diameter which decreases from the open end of the tapered sleeve towards its opposite end. In addition, the annular seal includes an O-ring of an elastomeric material sandwiched between inner and outer rings of metal.

This feature has been found not only to prevent the entry of foreign material into the handpiece, thereby substantially reducing the need for frequent cleaning, but also to produce a quieter operation of the dental handpiece during the high-speed rotation of the dental tool.

According to a further feature of the present invention, the clamping device, or dental handpiece, comprises a further spring between the inner end of the tapered collet and the inner end of the tapered sleeve, the further spring urging the tapered collet inwardly of the tapered sleeve. This feature has been found to better assure positive clamping of the dental tool to the dental handpiece.

According to a further feature, the coiled spring has one end anchored to the enlarged head of the tapered collet and its opposite end anchored to the tapered sleeve to prevent rotation of the tapered collet within the tapered sleeve. An alternative construction is also described wherein the clamping device further includes a pin passing through the tapered sleeve and received within the axial slit of the tapered collet to prevent rotation of the tapered collet within the tapered sleeve.

According to a still further feature in the present application, the tapered sleeve is carried by an air turbine rotatably mounted to the housing by a ball bearing assembly at the inner end of the tapered sleeve, and an air bearing assembly at the outer end of the tapered sleeve. Such a construction has also been found to produce a quieter, smoother operation at high speed.

According to a still further feature in the present application, the end of the dental handpiece opposite to that carrying the clamping device for the dental tool, is received within a push-pull connector of an air supply line for supplying pressurized air to the air turbine within the dental handpiece. The push-pull connector includes an inner sleeve, an outer sleeve manually movable in the axial direction over the inner sleeve, a ball carried by the inner sleeve, and a spring urging the outer sleeve over the ball to cause the inner surface of the outer sleeve to engage the ball and thereby to couple the dental handpiece to the air supply line, the outer sleeve being manually movable in the axial direction with respect to the inner sleeve to disengage from the ball and thereby to decouple the dental handpiece from the air supply line. The opposite end of the dental handpiece includes an annular recess receiving the ball carried by the push-pull connector to permit 360° swivelling of the dental handpiece with respect to the air supply line. Such a construction has been found to permit quick, convenient attachment and detachment of the dental handpiece to the air supply line, and also 360° swivelling of the dental handpiece with respect to the air supply line.

As will be more particularly apparent from the description below, such a clamping device, and particularly dental handpiece, can be constructed in the form of a simple, lightweight structure which is less tiresome for the operator to hold and which can be manipulated in a convenient manner for attaching thereto and removing therefrom various rodlike members, e.g. various dental tools to a dental handpiece.

Further features and advantages of the invention will be apparent from the description below.

BRIEF DESCRIPTION OF THE DRAWINGS

The invention is herein described, by way of example only, with reference to the accompanying drawings wherein.

DESCRIPTION OF PREFERRED EMBODIMENTS

Figure 1:
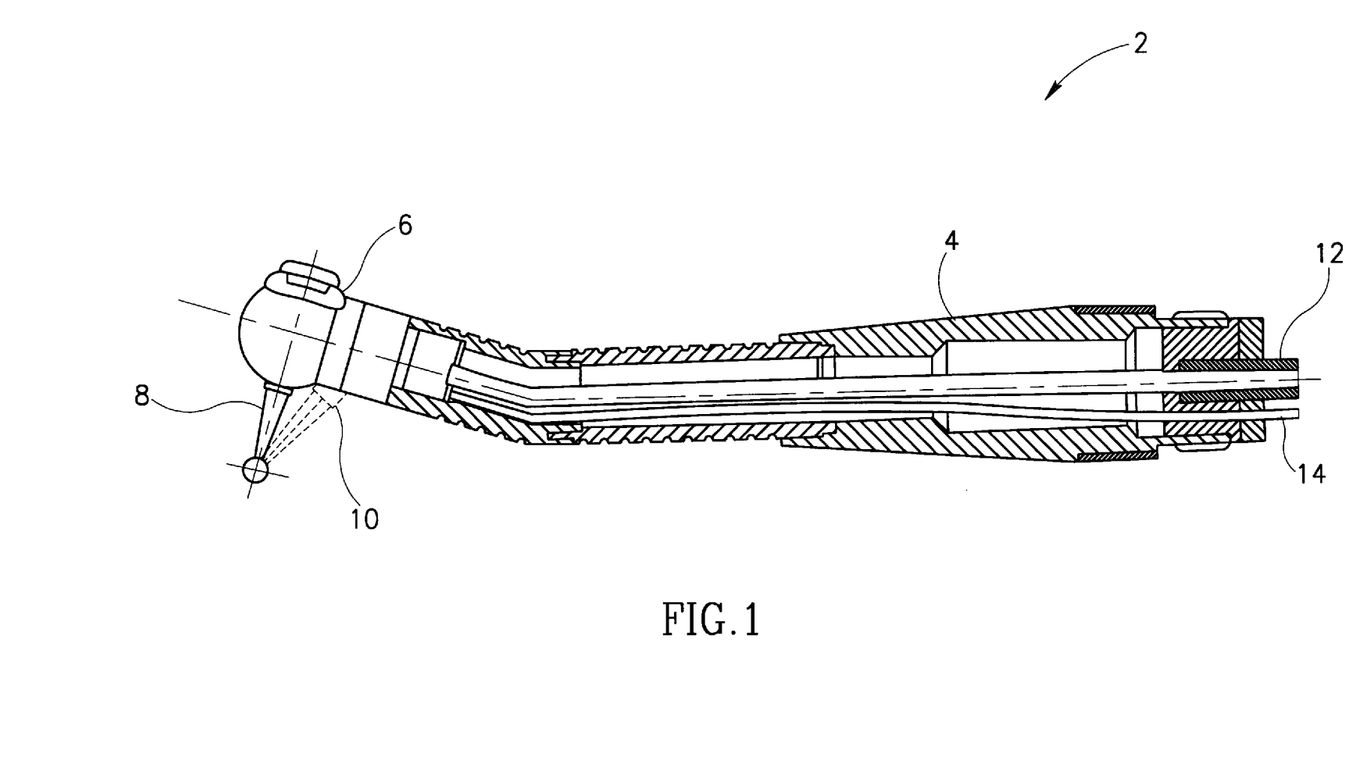
FIG. 1 is a longitudinal section view illustrating one form of dental handpiece constructed in accordance with the invention of my patent application Ser. No. 08/315,859.
Figure 2:
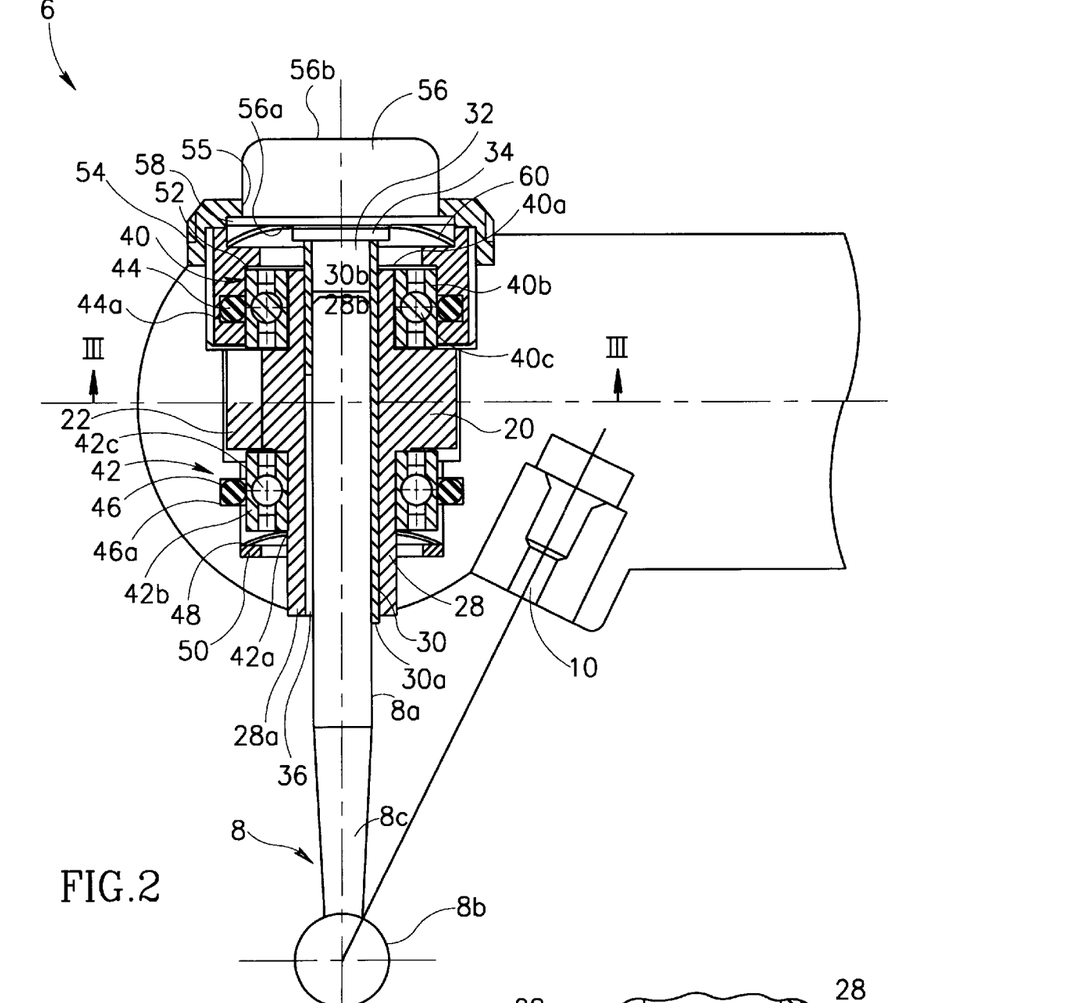
FIG. 2 is an enlarged sectional view illustrating the clamping device construction at the end of a handpiece for clamping shafts of various dental tools, FIG. 2a being an enlarged fragmentary view of FIG. 2.
Figure 3:
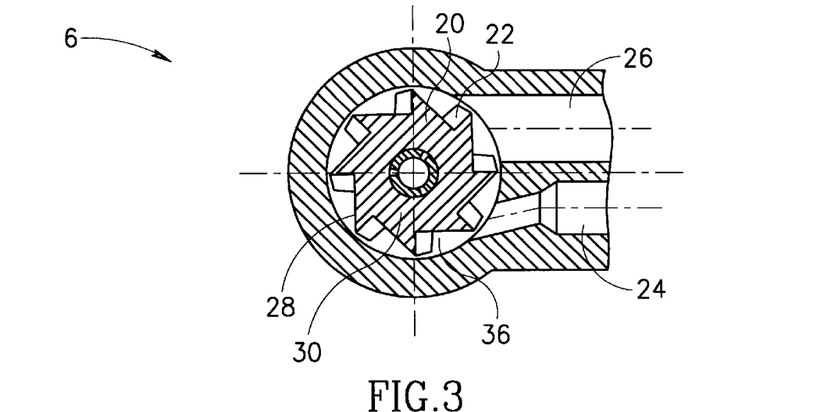
FIG. 3. is a section view along line III—III of FIG. 2.

The Embodiment of FIGS. 1–3

The dental handpiece of FIGS. 1–3 is that illustrated in my patent application Ser. No. 08/315,859. It includes a housing, generally designated 2, having a hand-gripping section 4 at one end, and a tool-holding section 6 at the opposite end for holding a dental tool 8, such as a bur or drill. section 6 of housing 2 is further formed with a water spray nozzle 10 for discharging a water spray onto the site being worked by the dental tool 8. The dental handpiece illustrated in FIG. 1 is an air turbine handpiece in which compressed air is supplied, via a conduit 12 at the back end of the handpiece, to an air turbine within housing section 6 to rotate the dental tool 8 at a very high speed, e.g. in the order of 400,000 rpm. The rear end of the dental handpiece includes a further conduit 14 for introducing the water discharged in the form of a spray via nozzle 10 onto the working site of the dental tool.

Such dental handpieces are well known, and therefore further details of its construction are not set forth herein. The remainder of the description will, therefore, be directed primarily to the construction of the housing section 6, and particularly to the clamping device within this housing section for clamping and removing the dental tool 8, as more particularly illustrated in FIGS. 2 and 3.

FIG. 2 shows, for purposes of example, the dental tool 8 as being of the bur type, including a shaft 8a of uniform diameter at one end, a bur 8b of spherical (or disc) shape at the opposite end, and a tapered juncture 8c between the shaft 8a and the bur 8b. It will be appreciated, however, that the dental tool 8 could be of another type, e.g., a drill carried at the end of the shaft.

As shown particularly in FIG. 3, housing section 6 includes an air turbine 20 formed with a plurality of blades 22 impinged by compressed air flowing from its inlet conduit 24 to its outlet conduit 26 in order to rotate the air turbine at a very high speed. Air turbine 20 is integrally formed with a sleeve 28 of tapered configuration. One end of sleeve 28 is open, as shown at 28a, for receiving the shaft 8a of the dental tool 8. The inner diameter of tapered sleeve 28 decreases from its open end 28a to its opposite end 28b, which is also open.

Figure 2A:
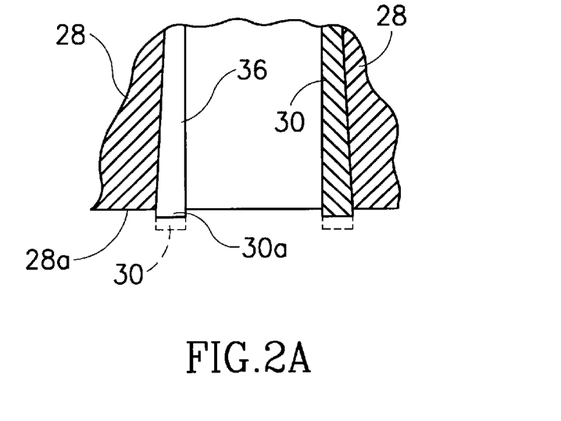

Tapered sleeve 28 which, as noted above, is integrally formed with the air turbine 20, receives a tapered collet 30. Tapered collet 30 is also formed with an open end 30a received within the open end 28a of the tapered sleeve 28 for receiving the shaft 8a of the dental tool 8. The outer diameter of tapered collet 30 decreases from its open end 30a to its opposite end 30b, as was particularly seen in FIG. 2a. Its opposite end 30b is closed by an end wall or plug 32 formed within an enlarged head 34.

Tapered collet 30 is further formed with three axial slits 36, equally-spaced around its circumference as shown in FIG. 3. Slits 36 start at its open end 30a and extend only for a part of the length of the collet towards opposite end 30b.

In the example illustrated in the drawings, slits 36 extend about two-thirds the length of the tapered collet 30. As will be described more particularly below, the slits 36 permit the respective section of the tapered collet to contract in order to firmly clamp therein the shaft 8a of the dental tool, or to expand in order to release the shaft for purposes of removing the dental tool or reinserting another dental tool in its place.

Housing section 6 further includes two ball bearing assemblies 40, 42, at the opposite sides of the axis of housing section 6 for rotatably mounting the air turbine 20, its tapered sleeve 28, the tapered collet 30, and the dental tool 8 when clamped therein, with respect to the housing. Thus, each ball bearing assembly 40, 42 includes: a rotary ring 40a, 42a; a static ring 40b, 42b; and a plurality of balls 40c, 42c interposed between both rings.

Housing section 6 further includes a vibration-absorbing O-ring 44, 46, for each of the ball bearing assemblies 40, 42. Each O-ring 44, 46 is received within an annular recess 44a, 46a, formed in housing section 6 and bearing against the static ring 40b, 42b, of the respective assembly.

Housing section 6 further includes a spring 48 bearing against a plastic ring 50 e.g. of "Teflon" (Reg T.M.) for preloading the static part of the bearing in order to reduce vibration during the high-speed rotation of the dental tool. A similar plastic ring 52 is provided at the opposite end of the housing section 6 cooperable with bearing assembly 40.

The latter end of housing section 6 is closed by a collar 54 treadedly attached to the housing section and formed with a central opening 55 in which a release button 56 is mounted to project through the opening. Button 56 is formed with an outwardly-projecting rim 58 around its circumference engageable by the edge of collar 54 circumscribing opening 55 receiving the button. An annular spring 60 is interposed between the housing section 6 and button 56. Spring 60 is engageable within inner surface 56a of the button to urge the button outwardly, limited by the engagement of rim 58 of the button with the undersurface of collar 54. Button 56, however, is depressible inwardly of the housing section 6 against spring 60, by pressing against the outer surface 56b of the button, to bring the inner surface 56a of the button into engagement with the enlarged head 34 of the tapered collet 30, and thereby to move the tapered collet outwardly of the tapered sleeve 28.

It will thus be seen that in order to remove the dental tool 8 from the housing section 6, the outer surface 56b of release button 56 is manually engaged to depress the button against the action of spring 60. This causes the inner surface 56a of button 56 to engage the enlarged head 34 of the tapered collet 30, and to move the tapered collet outwardly of the tapered sleeve 28, as shown by broken lines 30' in FIG. 2a. When this occurs, the slits 36 formed in the outer two-thirds section of the tapered collet 30 permit that section of the tapered collet, moving outwardly of the tapered sleeve 28 to expand and thereby to release the shaft 8a of the dental tool. The dental tool may then be manually grasped and removed from the tapered collet 30.

When it is desired to insert another dental tool 8, button 56 is again depressed to move the tapered collet 30 outwardly of the tapered sleeve 28, thereby providing a relatively large diameter for the tapered collet to receive the shaft 8a of the dental tool 8. While the button is still depressed, the dental tool is pushed inwardly into the tapered collet 30 until the end of the dental tool shaft 8a limits against the end wall 32 of the tapered collet. At that time, button 56 is released, whereupon spring 60 moves the button 56 slightly outwardly of the housing. The user then manually pushes the dental tool shaft 8a further inwardly into the housing. This also moves the tapered collet 30 and its projected end 30' (FIG. 2a) further into the housing, until the enlarged head 34 of the tapered collet limits against the inner surface 56a of the button 56, at which time the dental tool 8 is firmly clamped in housing section 6 by the wedging action between the tapered collet 30 and the tapered sleeve 28.

In a preferred construction, the tapered collet 30 and the tapered sleeve 28 both may have a taper of 1:40; the housing 4, including housing section 6, the air turbine 20 including its blades 22 and its tapered sleeve 28, and the tapered collet 30, may all be made of anodized aluminium; and both the inner and outer surfaces of the tapered collet 30 and the inner surface of the tapered sleeve 28 may be plated with hard electroless nickel.

Other Variations and Improvements

FIGS. 4–9a illustrate a number of variations or improvements in the structure of the dental handpiece of FIGS. 1–3. To facilitate understanding, those elements of the handpiece which are common to the elements described above with respect to FIGS. 1–3 carry the same reference numerals, and only the modified or new elements are described below.

Figure 4:
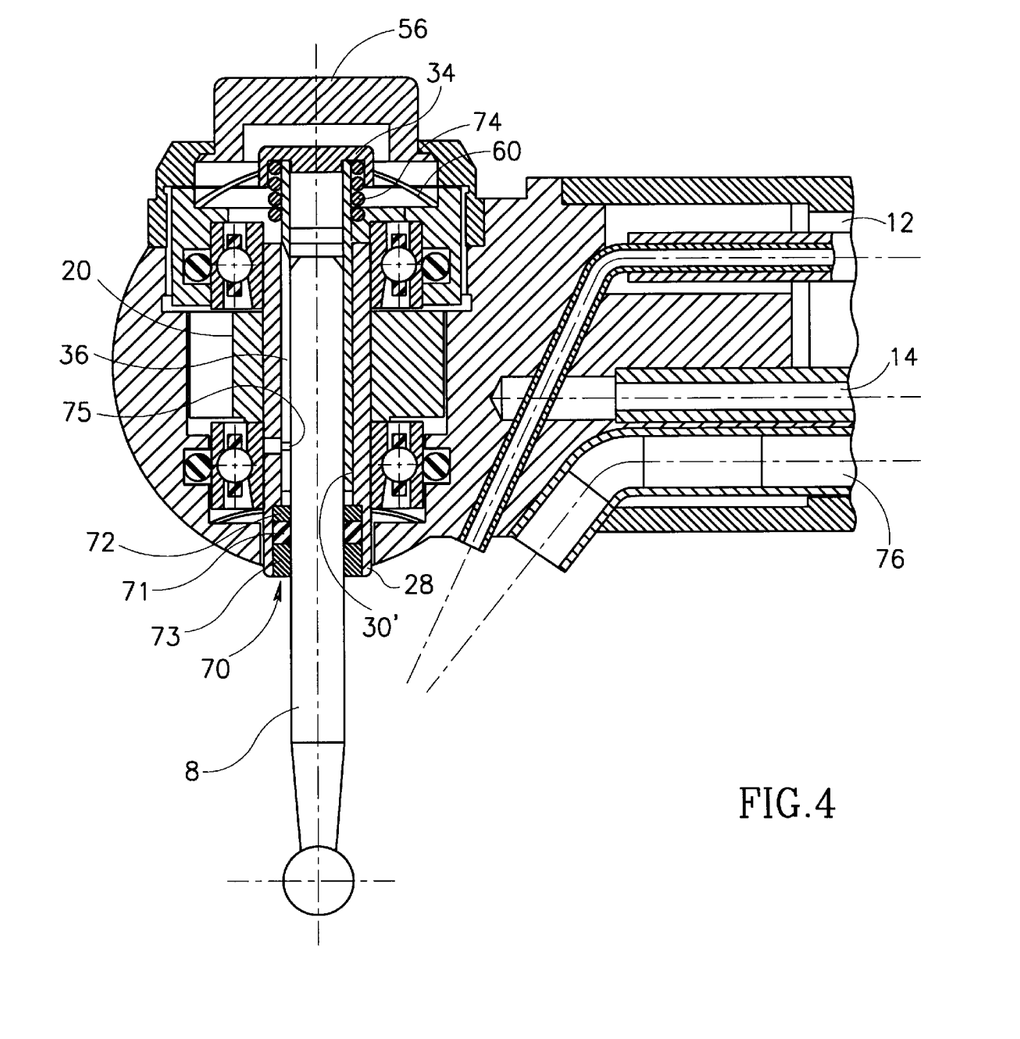
FIG. 4 is a view similar to that of FIG. 2 illustrating an improved construction in accordance with one aspect of the present invention.
Figure 5:
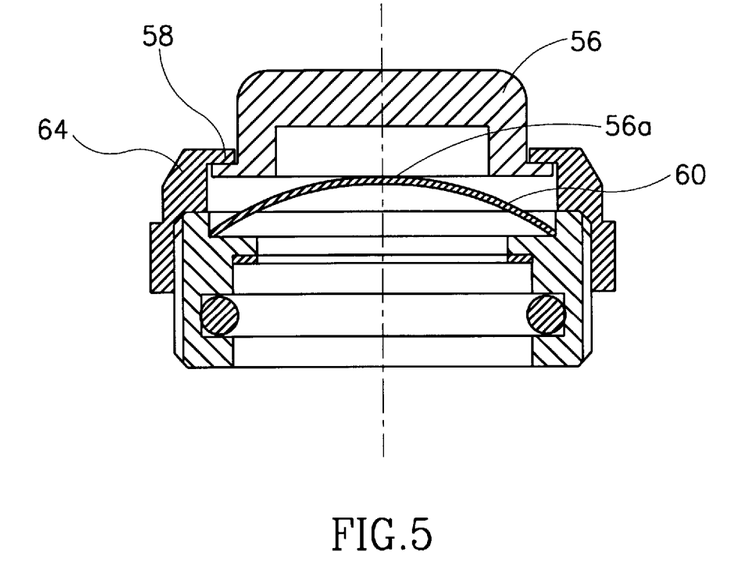
FIG. 5 is an enlarged fragmentary view more particularly illustrating the annular spring which urges the release button to its outer position.

FIGS. 4 and 5 illustrate one variation in the construction of the above-described handpiece 2. In this variation, the tapered collet, shown at 30', does not extend completely to the open end of the tapered sleeve 28, but rather terminates short of the open end of the tapered sleeve. In addition, an annular seal 70 is carried by the tapered sleeved 28 between its open end and the open end of the tapered collet 30'. Annular seal 70 is coaxial with the tapered sleeved 28 for receiving the dental tool 8.

Annular seal 70 includes an O-ring 71 of an elastomeric material sandwiched between an inner metal ring 72 and an outer metal ring 73. The annular seal 70 is wedged within the outer end of the tapered sleeve 28, with the outer diameters of the two metal rings 72, 73 decreasing from the open end of the sleeve towards its opposite end.

Such a construction prevents the entry of dirt within the housing, thereby reducing the need for frequent cleaning. In addition, it also absorbs vibrations of the dental tool during its high-speed rotation, thereby producing a quieter operation.

Another change included in the modification of FIGS. 4 and 5 is the provision of a coiled spring 74 between the enlarged head 34 at the inner end of the tapered collet 30' and the inner end of the tapered sleeve 28. Coiled spring 74 is in addition to the annular spring 60 interposed between the housing section 6 and the depressible button 56. Thus, as shown in FIG. 5, the annular spring 60 is engageable with the inner surface 56a of button 56, in the same manner as described above with respect to the construction of FIGS. 1–3, to urge the button outwardly, the outward movement of the button being limited by the engagement of rim 58 of the button with the undersurface of collar 54.

In the modified construction illustrated in FIG. 4, coiled spring 74 is provided in addition to the annular spring 60. Coiled spring 74 is a relatively light spring which urges the inner end of the tapered collet 30' inwardly of the tapered sleeve 28. Such a construction has been found to more positively assure that the tapered collet will be securely clamped within the tapered sleeve in case the user neglects to manually push the dental tool shaft 8a further inwardly into the housing, after button 56 has been released as described above. If this should occur, coiled spring 74 will start the inward movement of the collet, which inward movement will be completed by the normal use of the dental device.

A further change included in the modification illustrated in FIG. 4 is the addition of a pin 75 passing through the tapered sleeve 28 and received within one of the three axial slits 36 of the tapered collet 30'. Pin 75 more securely holds the tapered collet 30' against rotational movement within the tapered sleeve 28.

A further change in the modification illustrated in FIG. 4 is the provision of a light-guide conduit 76 in the dental handpiece for receiving an optical fiber in order to illuminate the working area of the dental tool. Light conduit 76 is in addition to the air conduit 12 for supplying air to the turbine 20, and in addition to the water conduit 14 for supplying water which is discharged in the form of a spray via nozzle 10 (FIG. 2) onto the working area of the dental tool.

Figure 6:
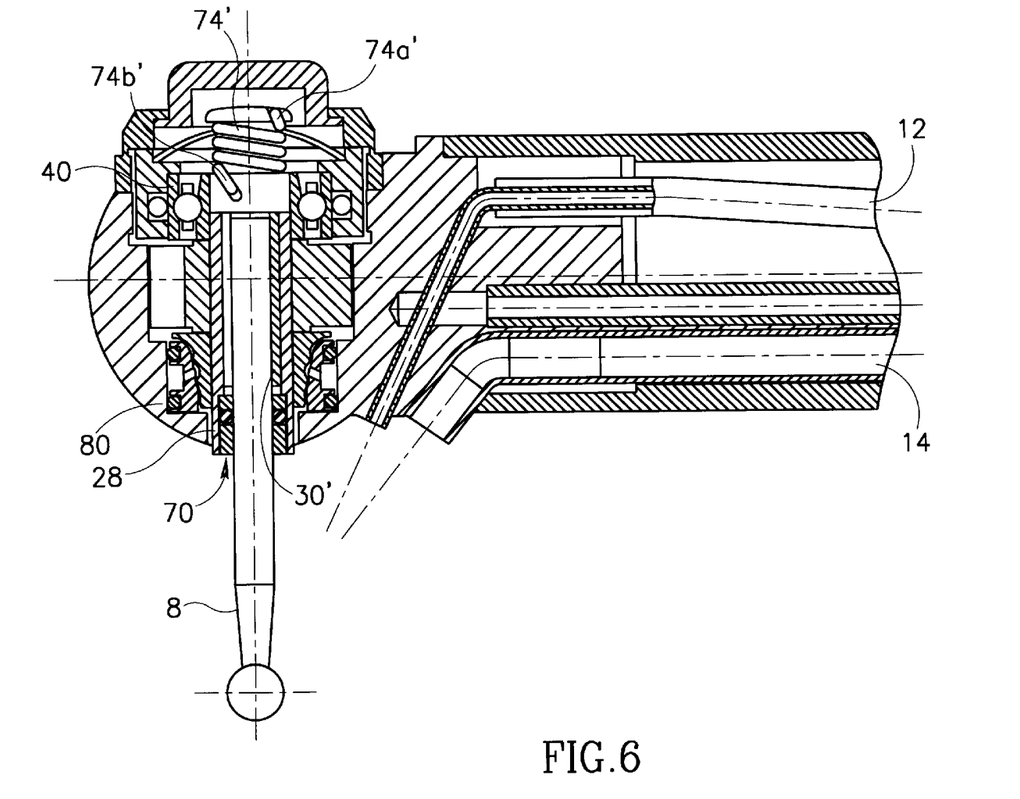
FIG. 6 is a view similar to that of FIGS. 2 and 4 illustrating a variation in the construction of the clamping device.
Figure 6A:
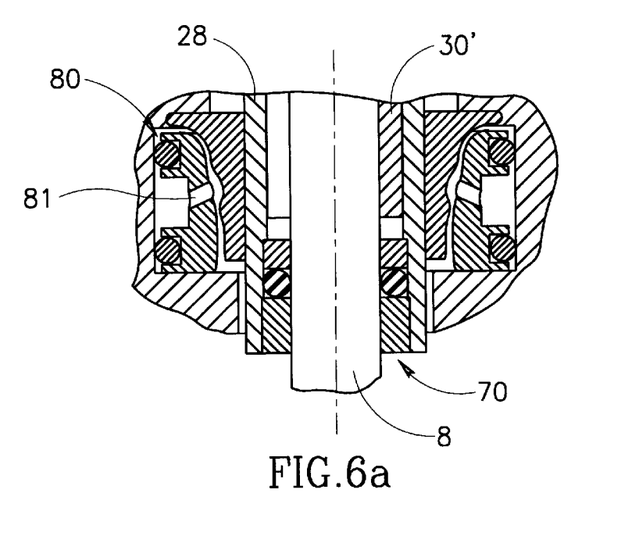
FIG. 6a is an enlarged fragmentary view of a portion of FIG. 6, showing particularly the air bearing.

FIGS. 6 and 6a illustrate a further modification in the dental handpiece. One change in this modification is in the construction of the coiled spring, therein shown as 74', which urges the tapered collet 30' inwardly of the tapered sleeve 28. In the modification illustrated in FIG. 6, the coiled spring 74' has one end 74a' anchored to the enlarged head 34 of the tapered collet 30', and its opposite end 74b' anchored to the tapered sleeve 28. Thus, coiled spring 74' in FIG. 6 also serves the function of preventing rotation of the tapered collet within the tapered sleeve, and thereby eliminates the need for the pin 75 provided in the construction illustrated in FIG. 4 for this purpose.

Another change in the modification illustrated in FIG. 6 is the substitution of an air bearing assembly, shown at 80, for the outer ball bearing assembly 42 in the construction illustrated in FIG. 2. Thus, the dental handpiece illustrated in FIG. 6 also includes the inner ball bearing assembly 40 as in the construction illustrated in FIG. 2, but the outer ball bearing assembly 42 of FIG. 2 is replaced by the air bearing assembly 80. As shown particularly in FIG. 6a, the air bearing assembly 80 is formed with a plurality of oblique openings 82 receiving air from the air turbine 20 which produces an air pressure to preload the static part of the roller bearing assembly 40 and thus reduces vibrations during the high-speed rotation of the dental tool. The air bearing assembly 80 accordingly replaces the spring 48 and plastic ring 50 in the construction illustrated in FIG. 2.

Figure 7:
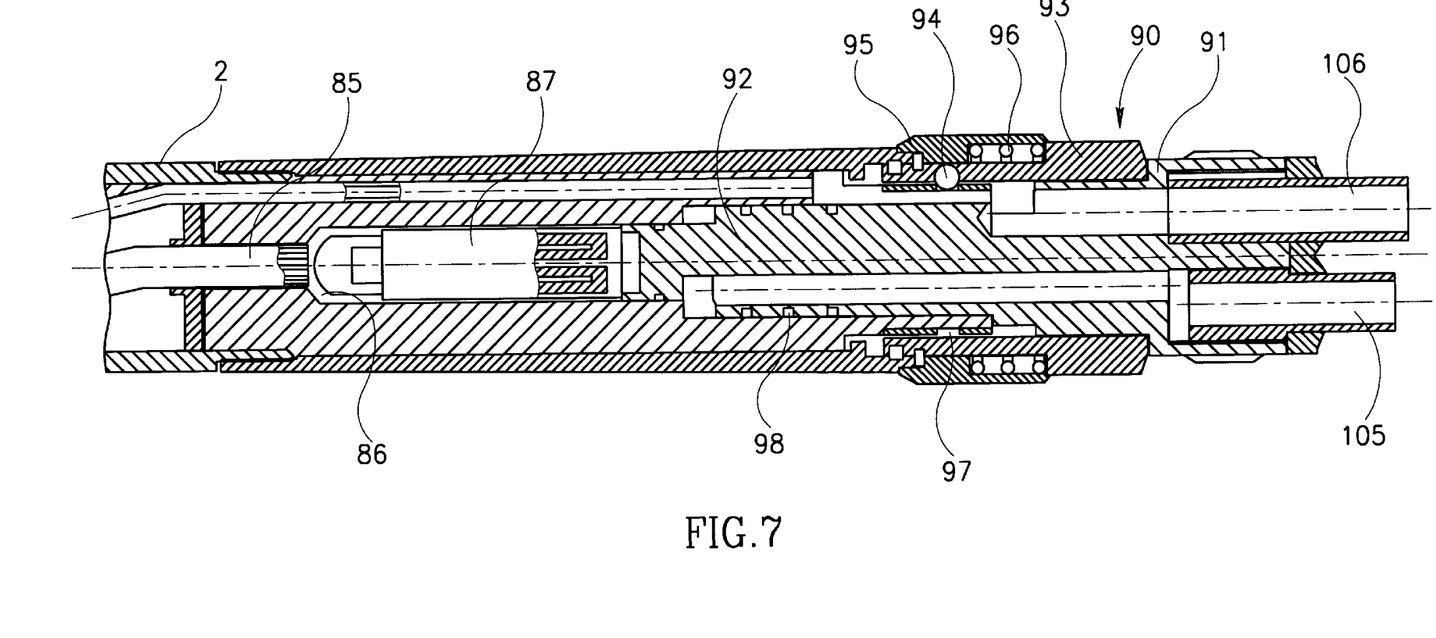
FIG. 7 is a longitudinal sectional view illustrating the end of the dental handpiece connectible to the air supply line and the push-pull connector used for that purpose.

FIG. 7 illustrates the opposite end of the dental handpiece 2 and a connector for connecting the handpiece to the air supply for supplying air to the air conduit 12 (FIG. 1), and for supplying water to the water conduit 14. In the construction illustrated in FIG. 7, the handpiece also includes an optical fiber 85 at one end of a cavity 86 formed in the handpiece for receiving a light bulb 87 in the connector to the air and water supply.

Figure 8:
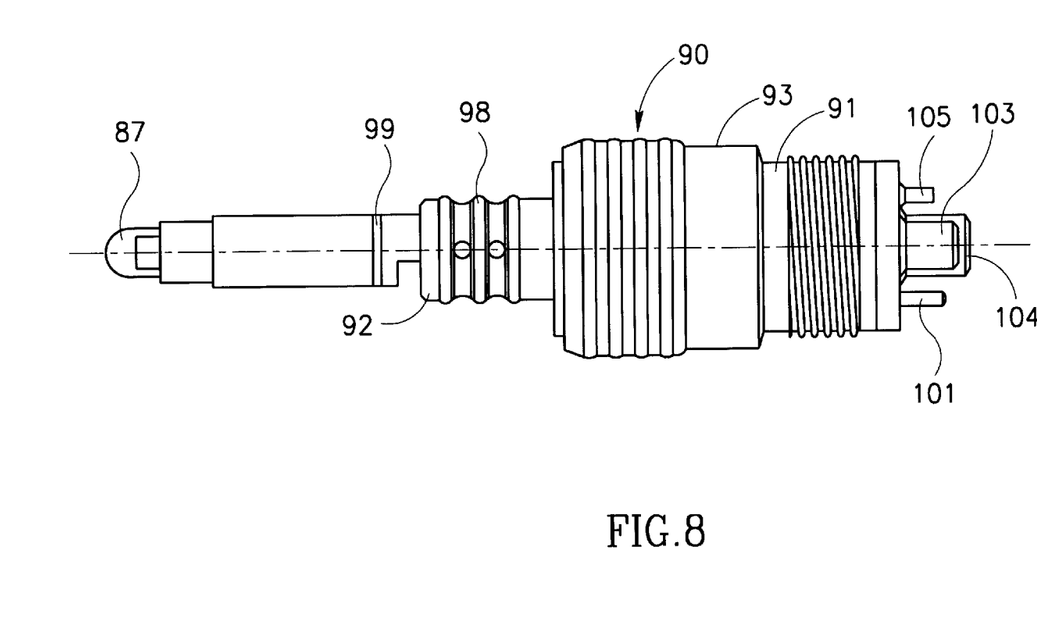
FIG. 8 is an end elevational view illustrating the push-pull connector of FIG. 7.
Figure 9:
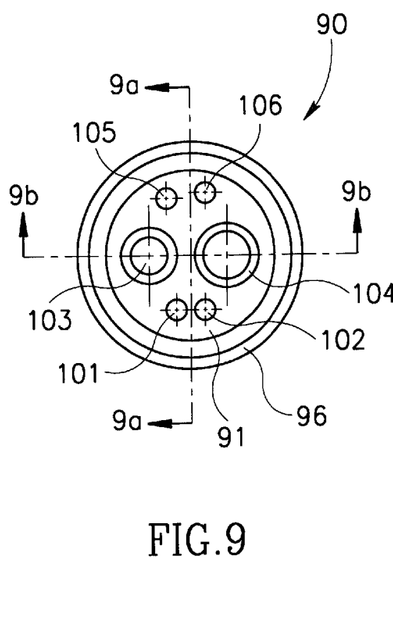
FIG. 9 is an end view of the push-pull connector of FIG. 8.
Figure 9A:
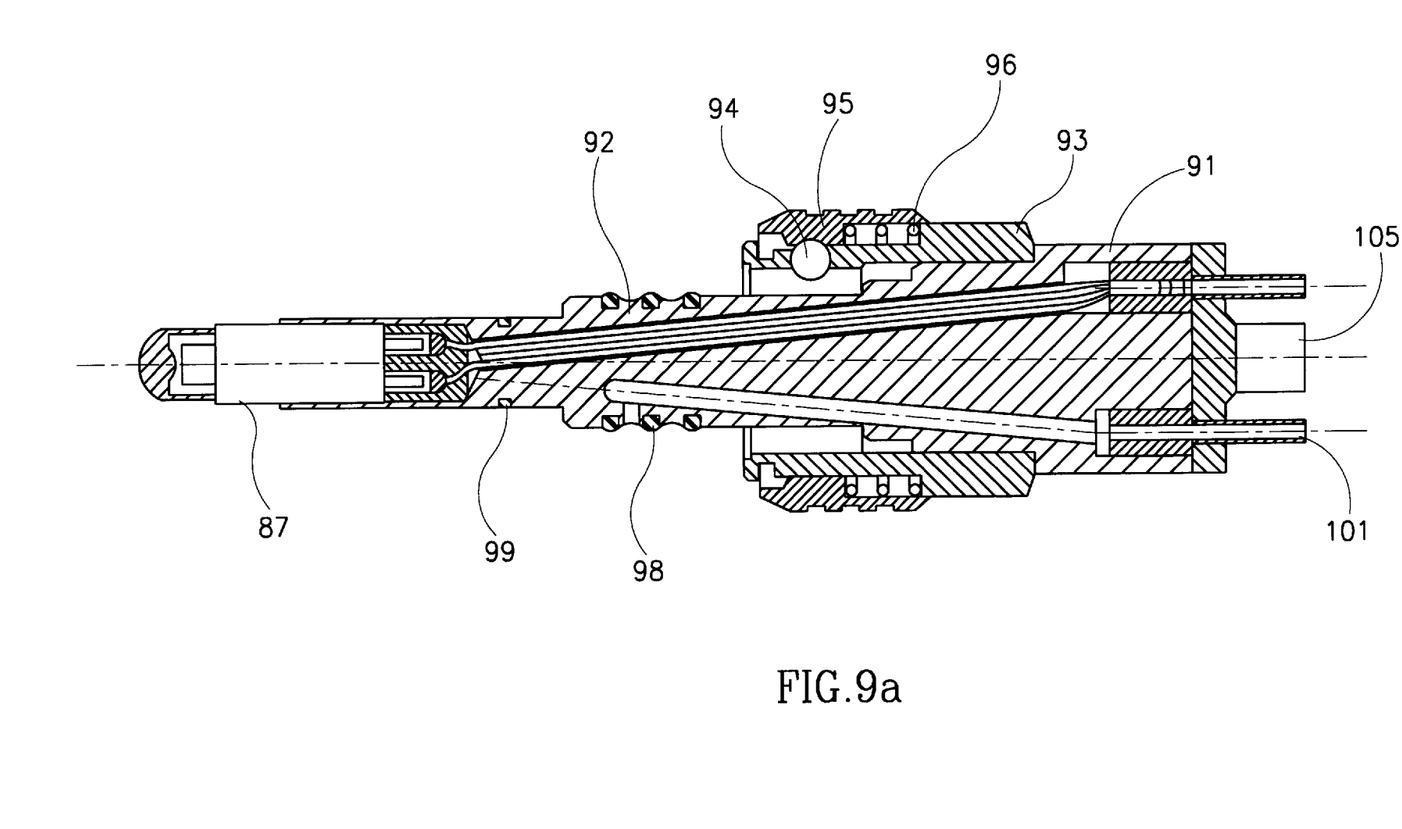
FIG. 9a is a sectional view along line IXA—IXA of FIG. 9.

The connector to the air and water supply is generally designated 90 and is more particularly illustrated in FIGS. 8 and 9. It is a push-pull connector which permits convenient, quick connection to the handpiece by a simple push-pull operation. It also is a swivel connector which permits the handpiece to be completely rotated 360° with respect to the connector and to the air and water supply line to which the connector is attached.

Figure 9B:
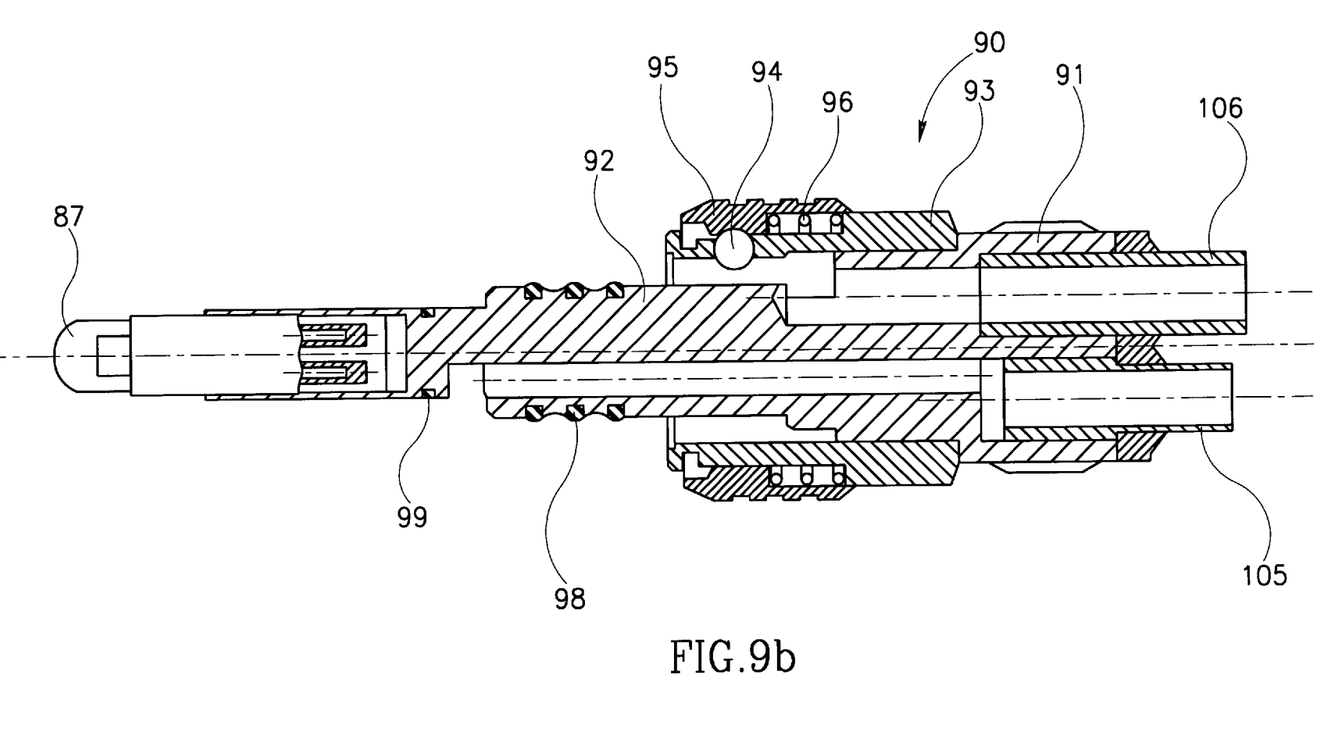
FIG. 9b is a sectional view along line IXB—IXB of FIG. 9.

Thus, as shown in FIGS. 7–9, the push-pull connector 90 includes a housing 91 formed with a stem 92 receivable within cavity 86 of the handpiece 2. Connector 90 further includes an inner sleeve 93, a ball 94 received within a hole in sleeve 93, and an outer sleeve 95 overlying ball 94. A spring 96 between the two sleeves 93 and 95 normally urges the outer sleeve 95 to the position illustrated in FIGS. 9a and 9b, overlying ball 94, and thereby preventing the ball from moving radially outwardly with respect to its hole in the inner sleeve 93. This is the locking position of the outer sleeve 95. The outer sleeve 95, however, may be manually moved in the axial direction, against the force of spring 96, to cause the undersurface of the outer sleeve to clear ball 94, and thereby to permit the ball to move radially outwardly with respect to the inner sleeve 93.

When the connector 90 is received within cavity 86 of the handpiece 2, ball 94 is receivable with an annular recess 97 (FIG. 7) formed in that end of the handpiece. Ball 94, when so received within annular recess 97, permits the handpiece to swivel 360° with respect to the connector and also locks the connector to the handpiece. When it is desired to detach the connector from the handpiece, the outer sleeve 95 is manually moved (rightwardly in FIG. 7), against the action of spring 96, permitting the ball 94 to move outwardly of annular recess 97, and thereby to permit detachment of the connector from the handpiece.

Stem 92 includes a plurality (three in this case) of O-rings 98 axially spaced from each other and engageable with the inner surface of handpiece 2 around its cavity 86 to seal the connector with respect to the handpiece, while permitting the above-described swivel movement of the handpiece. Stem 92 includes a socket for bulb 87 in alignment with optical fiber 85 of the handpiece. A fourth O-ring 99, of smaller diameter than O-rings 98, is provided around the outer surface of the end of stem 92 receiving the light bulb 87.

As shown particularly in FIG. 9, the opposite end of connector 90 includes electrical terminals 101, 102 for providing electricity to the light bulb 87, an inlet terminal 103 and an outlet terminal 104 for the air supplied to the air turbine 20, a water terminal 105 for supplying water to the water conduit 14, and an air terminal 106 for supplying air to be mixed with the water discharged in the form of a spray from nozzle 10 (FIG. 2).

If the connector 90 is to be used with a handpiece not provided with an optical fiber light guide, the light bulb 87 would of course be omitted.

While the invention has been described with respect to several preferred embodiments, it will be appreciated that many other variations, modifications and applications of the invention may be made.

I claim:

1. A clamping device for clamping a rodlike member to a housing, comprising:

a taper ed sleeve carried by s aid housing and having an inner diameter which decreases from an open end thereof to its opposite end;

a tapered collet received within said open end of the tapered sleeve; said tapered collet having an inner end and an open end for receiving the rodlike member, and an outer diameter which decreases from its open end to its opposite end; said tapered collet being formed with an axial slit starting from its open end and extending along at least a part of its length, permitting said part to contract in diameter in order to firmly clamp the rodlike member when received in the tapered collet and the tapered collet is received within the tapered sleeve;

a depressible button carried by said housing and having an inner surface engageable with said opposite end of the tapered collet, and an outer surface engageable by a user to depress the button;

a spring normally urging said button outwardly of the housing but being depressible to move the tapered collet outwardly of the tapered sleeve, thereby to expand said part of the tapered collet to permit removal of the rodlike member from the tapered collet, or insertion of the rodlike member into the tapered collet and firm clamping of the rodlike member in the tapered collet by manually pressing the rodlike member and tapered collet into the tapered sleeve;

the open end of said tapered collet terminating short of the open end of said tapered sleeve;

and an annular seal carried by said tapered sleeve between its open end and the open end of said tapered collet, said annular seal being coaxial with said tapered sleeve for receiving said rodlike member.

2. The clamping device according to claim 1, wherein said annular seal is wedged within the outer end of said tapered sleeve and has an outer diameter which decreases from the open end of the tapered sleeve towards its opposite end.

3. The clamping device according to claim 1, wherein said annular seal includes an O-ring of an elastomeric material sandwiched between inner and outer rings of metal.

4. The clamping device according to claim 1, wherein the clamping device further comprises a further spring between the inner end of said tapered collet and the opposite end of said tapered sleeve, said further spring urging said tapered collet inwardly of the tapered sleeve.

5. The clamping device according to claim 4, wherein said further spring is a coiled spring and is interposed between an enlarged head carried by the inner end of the tapered collet and an inner face of said tapered sleeve.

6. The clamping device according to claim 5, wherein said coiled spring has one end anchored to said enlarged head of the tapered collet and its opposite end anchored to said tapered sleeve to prevent rotation of said tapered collet within said tapered sleeve.

7. The clamping device according to claim 1, wherein the clamping device further includes a pin passing through said tapered sleeve and received within said axial slit of the tapered collet to prevent rotation of said tapered collet within said tapered sleeve.

8. The clamping device according to claim 1, wherein said tapered sleeve is carried by an air turbine rotatably mounted to said housing by a ball bearing assembly at said opposite end of the tapered sleeve, and an air bearing assembly at said open end of the tapered sleeve.

9. The clamping device according to claim 1, wherein said housing is at one end of a dental handpiece for clamping the rodlike shaft of a dental tool, said dental handpiece including an air turbine for rotating said dental tool.

10. The clamping device according to claim 9, wherein the end of said dental handpiece opposite to that clamping said distal tool is received within a connector of an air supply line for driving said air turbine.

11. The clamping device according to claim 10, wherein said connector is a push-pull connector and includes an inner sleeve, an outer sleeve manually movable in the axial direction over the inner sleeve, a ball carried by the inner sleeve, and a spring urging said outer sleeve over said ball to cause the inner surface of the outer sleeve to engage the ball and thereby to couple the dental handpiece to said air supply line, said outer sleeve being manually movable in the axial direction with respect to said inner sleeve to disengage from said ball and thereby to decouple the dental handpiece from said air supply line.

12. The clamping device according to claim 11, wherein said opposite end of the dental handpiece includes an annular recess receiving said ball carried by said push-pull connector to permit 360° swivelling of the dental handpiece with respect to said air supply line.

13. The clamping device according to claim 12, wherein said push-pull connector further includes a stem receivable within a cavity formed in said opposite end of the dental handpiece, said stem including at least one annular sealing ring on its outer face engageable with the surface of said cavity for sealing the push-connector with respect to the dental handpiece.

14. The clamping device according to claim 12, wherein said stem further includes a light source for illuminating one end of an optical fiber carried by said opposite end of the dental handpiece, the opposite end of said optical fiber being located to illuminate the working area of said dental tool.

15. A clamping device for clamping a rodlike member to a housing, comprising:

a tapered sleeve carried by said housing and having an inner diameter which decreases from an open end thereof to its opposite end;

a tapered collet received within said open end of the tapered sleeve; said tapered collet having an open end for receiving the rodlike member, and an outer diameter which decreases from its open end to its opposite end; said tapered collet being formed with an axial slit starting from its open end and extending along at least a part of its length, permitting said part to contract in diameter in order to firmly clamp the rodlike member when received in the tapered collet and the tapered collet is received within the tapered sleeve;

a depressible button carried by said housing and having an inner surface engageable with said opposite end of the tapered collet, and an outer surface engageable by a user to depress the button;

a spring normally urging said button outwardly of the housing but being depressible to move the tapered collet outwardly of the tapered sleeve, thereby to expand said part of the tapered collet to permit removal of the rodlike member from the tapered collet, or insertion of the rodlike member into the tapered collet and firm clamping of the rodlike member in the tapered collet by manually pressing the rodlike member and tapered collet into the tapered sleeve;

and a further spring between an inner end of said tapered collet and said opposite end of said tapered sleeve, said further spring urging said tapered collet inwardly of the tapered sleeve.

16. The clamping device according to claim 15, wherein said further spring is a coiled spring and is interposed between an enlarged head carried by the inner end of the tapered collet and said opposite face of said tapered sleeve.

17. The clamping device according to claim 16, wherein said coiled spring has one end anchored to said enlarged head of the tapered collet and its opposite end anchored to said tapered sleeve to prevent rotation of said tapered collet within said tapered sleeve.

18. The clamping device according to claim 15, wherein said tapered sleeve is carried by an air turbine rotatably mounted to said housing by a ball bearing assembly at said opposite end of the tapered sleeve, and an air bearing assembly at the open end of the tapered sleeve.

19. A clamping device for clamping a rodlike member to a housing, comprising:

a tapered sleeve carried by said housing and having an inner diameter which decreases from an open end thereof to its opposite end;

a tapered collet received within said open end of the tapered sleeve; said tapered collet having an open end for receiving the rodlike member, and an outer diameter which decreases from its open end to its opposite end; said tapered collet being formed with an axial slit starting from its open end and extending along at least a part of its length, permitting said part to contract in diameter in order to firmly clamp the rodlike member when received in the tapered collet and the tapered collet is received within the tapered sleeve;

a depressible button carried by said housing and having an inner surface engageable with said opposite end of the tapered collet, and an outer surface engageable by a user to depress the button;

a spring normally urging said button outwardly of the housing but being depressible to move the tapered collet outwardly of the tapered sleeve, thereby to expand said part of the tapered collet to permit removal of the rodlike member from the tapered collet, or insertion of the rodlike member into the tapered collet and firm clamping of the rodlike member in the tapered collet by manually pressing the rodlike member and tapered collet into the tapered sleeve;

and a pin passing through said tapered sleeve and received within said axial slit of the tapered collet to prevent rotation of the tapered collet within said tapered sleeve.

20. The clamping device according to claim 19, wherein said tapered sleeve is carried by an air turbine rotatably mounted to said housing by a ball bearing assembly at said opposite end of the tapered sleeve, and an air bearing assembly at said open end of the tapered sleeve.

* * * * *